US006326050B1

(12) United States Patent
Goto et al.

(10) Patent No.: US 6,326,050 B1
(45) Date of Patent: *Dec. 4, 2001

(54) OIL OR FAT COMPOSITION CONTAINING PHYTOSTEROL

(75) Inventors: Naohiro Goto; Tsutomu Nishide; Yukitaka Tanaka; Takuji Yasukawa; Kenji Masui, all of Ibaraki (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/648,546

(22) Filed: Aug. 28, 2000

Related U.S. Application Data

(63) Continuation of application No. 09/069,754, filed as application No. PCT/JP98/02228 on May 21, 1998, now Pat. No. 6,025,348, which is a continuation of application No. 09/251,430, filed on Feb. 17, 1999, now Pat. No. 6,139,897.

(30) Foreign Application Priority Data

Mar. 24, 1998 (JP) .................................................... 10-75898

(51) Int. Cl.[7] .............................. A23D 9/07; A61K 31/56; A21K 31/235
(52) U.S. Cl. .......................... 426/601; 426/590; 426/611; 514/182; 514/533; 514/824; 424/439
(58) Field of Search ...................................... 426/601, 611, 426/590; 435/134; 424/439; 514/182, 533, 824

(56) References Cited

U.S. PATENT DOCUMENTS

| 5,244,887 | * | 9/1993 | Straub | 426/541 |
| 5,498,434 | * | 3/1996 | Johnston | 426/541 |
| 5,855,944 | * | 1/1999 | Koschinski | 426/541 |
| 5,912,042 | * | 6/1999 | Cain | 426/601 |
| 5,998,396 | * | 12/1999 | Nakano | 514/182 |
| 6,025,348 | | 2/2000 | Goto et al. . | |
| 6,139,897 | | 10/2000 | Goto et al. . | |

FOREIGN PATENT DOCUMENTS

WO98/19556  *  5/1998  (WO).

* cited by examiner

Primary Examiner—Carolyn Paden
(74) Attorney, Agent, or Firm—Oblon, Spivak, McClelland, Maier & Neustadt, P.C.

(57) ABSTRACT

An oil or fat composition comprising an oil or fat comprising 15 wt. % or more of a diacylglycerol and 1.2 to 20 wt. % of phytosterol, dissolved or dispersed in the fat and oil is provided here, which can be used in the same way as usual oil and fat in daily life to reduce a hemal cholesterol value of a person having a high value of cholesterol and to raise no problem in appearance, taste, heating cooking and the like in comparison with usual edible oil and fat.

17 Claims, No Drawings

OIL OR FAT COMPOSITION CONTAINING PHYTOSTEROL

This application is a continuation of U.S. application Ser. No. 09/069,754, filed Apr. 30, 1998, now U.S. Pat. No. 6,025,348, which was the National Stage of International Application No. PCT/JP98/02228, filed May 21, 1998 which is a continuation of 09/251,430, filed Feb. 17, 1999, now U.S. Pat. No. 6,139,897.

BACKGROUND OF THE INVENTION

1. Field of the Invention

The present invention relates to an oil and fat composition which, when used in daily life similarly to ordinary fats, can lower the blood cholesterol level of a person having a high cholesterol level. It further relates to a food, a drink and a pharmaceutical preparation each containing the oil and fat composition.

2. Prior Arts

Phytosterol is found to be an effective basic material to reduce a hemal (in blood) cholesterol. It is included in vegetable seads. A usual, edible vegetable oil includes about 0.1 to 1.0 wt. % of it.

JP-A 10-179086 (EP-A 839 458) discloses food and drink in which phytosterol is soluble in oil by adding a large amount of vitamin E and an emulsifier. JP-B 56-14087 discloses a process for preparing a filler for soft capsules comprising an oily solvent being compatible with a soy bean residue principally comprising phytosterol. JP-B 6-59164 discloses use as a food additive of a sterine-containing composition of gel type comprising a lipophilic emulsifier having an HLB of less than 8 and an oil or fat being liquid at a normal temperature. Those publications disclose a diacylglycerol as an emulsifier. U.S. Pat. No. 5,843,499 discloses use of a corn fiber oil (about 73% of oil or fat, 6% of diacylglycerol, 4% of free sterol, 14% of sterol ester) as an additive to supplementary food to reduce cholesterol. WO98/01461 discloses application to a medicine of an organic metal complex obtained by reacting a trace amount of a di- or more valent metal ion being useful as a catalyst for metabolism and a trace amount of 1,2-diglyceride with phytostetrol.

The compositions of the above discussed prior arts, however, include too small an amount of diacylglycerols to effect an improved metabolism rate of fats. They include a large amount of vitamin E and a food additive of water-including gel, which cannot be taken similarly to fat in daily life.

SUMMARY OF THE INVENTION

The object of the present invention is to provide an oil and fat composition which lowers the blood cholesterol level of a person having a high cholesterol level when ingested in daily life similarly to ordinary fats and is usable without posing any problem concerning appearance, flavor, heat cooking, etc. when compared with general edible fats. It is to further provide a pharmaceutical preparation, food or drink containing the fat composition.

The present inventors have found that an oil and fat composition obtained by dissolving or containing a phytosterol in a fat comprising one or more specific polyhydric alcohol/fatty acid esters and its use in a manner similar to ordinary edible fats that enables a blood cholesterol concentration to be lowered, and accomplished the present invention.

When a phytosterol is ingested together with cholesterol competitive micelle formation occurs in the small intestine to reduce cholesterol absorption into the body and thus lower the blood cholesterol level. It is therefore important that for heightening the micelle formation by a phytosterol in the small intestine, the phytosterol be dissolved in a fat to be ingested.

The co-inventors of the application have studied these points and found that, when phytosterol is dissolved or dispersed in oil or fat including a large amount of a diacylglycerol, in particular diacylglycerols principally comprising a 1,3-diacylglycerol which is recognized to inhibit in effect accumulation of body fat, phytosterol, even having been crystallized, can be easily dissloved in body and will have an improved effect as such.

The invention provides an oil or fat composition comprising an oil or fat comprising 15 wt. % or more of a diacylglycerol and 1.2 to 20 wt. % of phytosterol, dissolved or dispersed in the fat and oil. The amount of the diacylglycerol of the oil or fat may range from 15 to 95 wt. %, preferably from 30 to 95 wt. %, more preferably from 55 to 95 wt. %, sepecifically preferably from 80 to 95 wt. %. The amount of phytosterol may range from 1.2 to 10 wt. %, preferably from 1.2 to less than 5 wt. %, more preferably from 1.2 to 4.7 wt. %.

The invention provides an oil or fat composition, being lightly colored, comprising an oil or fat comprising 80 wt. % or more of a diacylglycerol, obtained by hydrolyzing fats and oils, distilling the hydrolyzation product to produce fatty acids and glycerin and esterifying them in the presence of an enzyme, and 0.05 to 20 wt. % of phytosterol, dissolved or dispersed in the fat and oil. The amount of phytosterol of the composition may range from 0.05 to 10 wt. %, preferably from 0.05 to less than 5 wt. %, more preferably from 0.05 to 4.7 wt. %.

In both above shown compositions, a ratio of the free to the ester of the phytosterol is preferably 0.25 or more. The fatty acids comprised by the diacylglycerol preferably include 55 wt. % or more of unsaturated fatty acids, more preferably 70 wt. % or more. Specifically it is preferably composed of 20 to 65 wt. % of oleic acic and 15 to 65 wt. % of linoleic acid.

The invention provides a table cooking oil comprising an oil or fat composition as defined above, a food product including the oil or fat composition as defined above, a hemal (blood) cholesterol-reducing pharmaceutical preparation including the oil or fat composition as defined above, an oil or fat-processed food product 3 to 95 wt. % of oil or fat comprising 15 wt. % or more of a diacylglycerol and 1 to 20 wt. % of phytosterol and a beverage product comprising 0.2 to 10 wt. % of an oil or fat comprising 15 wt. % or more of a diacylglycerol and 0.2 to 1 wt. % of phytosterol.

The invention provides also a method of reducing a hemal cholesterol value comprising administering the oil or fat composition as defined above to a person and use of the oil or fat composition as defined above for manufacturing a hemal cholesterol-reducing pharmaceutical preparation.

Since such diacylglycerols as contained in a fat in an amount of 15% by weight or larger improve solubility of a phytosterol in particular as shown in the following Table 1, they can be incorporated into a fat in an amount of 15% by weight or larger, preferably 30% by weight or larger, more preferably 55% by weight or larger, especially preferably 80% by weight. When a larger amount of diacylglycerol is used in combination with phytosterol, a synergistic effect on lipid metabolism is expected.

However, it is preferred that the diacylglycerols be used in an amount of not more that 95% by weight from the viewpoint of cost performance.

Diacylglycerols suitable for use in this invention are those in which the constituent fatty acids comprise $C_{8-22}$ saturated fatty acids or unsaturated fatty acids. Since the oil and fat composition of this invention can be used similarly to generally edible fats, it is preferred to use diacylglycerols in which at least 55% by weight, more preferable at least 70% by weight, of the constituent fatty acids are accounted for by unsaturated fatty acids. A larger proportion of the diacylglycerols having such unsaturated fatty acid groups are liquid at least at human body temperature, whereby a lipid metabolism effect attributable to the dissolution of a phytosterol can be expected. In particular, unsaturated fatty acids composed of 20 to 65% by weight of oleic acid and 15 to 65% by weight of linoleic acid are preferable.

The diacylglycerol can be obtained by (1) interesterifying an oil or fat with glycerin or (2) esterifying an fatty acid with glycerin. These reactions may be effected either chemically with a hydroxide catalyst of an alkali metal, alkaline earth metal or enzymatically.

A diacylglycerol having an industrially high purity can be preferably manufactured by (2) the enzymatic method because (1) the chemical method easily degrades quality of the oil or fat such as coloring.

① An fatty acid obtained by steam-decomposing an oil or fat at 250 to 260° C. and distilling the decomposition product, ② a partial hydrolysis product obtained by steam-decomposing an oil or fat at 200 to 240° C. or ③ a partial hydrolysis product obtained by decomposing an oil or fat by an enzymatic method at 20 to 70° C. may be used as the starting fatty acid In any method, 20 to 80 parts by weight of water is added to 100 parts by weight of oil and fat so as to conduct decomposition reaction.

The fatty obtained this way can be esterified in the presence of a 1-, 3-position-selective lipase under dehydration to obtain a diacylglycerol (comprising less than 20 wt. % of triglycerides and less than 5 wt. % of monoglycerides), having a high purity of 80 wt. % or more, being lightly colored, with a little change in color (having a value of 10R+Y of 20 or less according Lovibond Method).

The oil or fat for use in this invention is not particularly limited as long as it is a generally edible oil or fat. Examples thereof include natural animal and vegetable oils and fats and processed fats obtained from these through transesterification, hydrogenation, fractionation, etc. Preferably used are vegetable oils such as soybean oil, rapeseed oil, rice bran oil, corn oil, and palm oil and processed fats obtained therefrom.

The phytosterol for use in the present invention is not particularly limited. Preferred examples thereof include α-sitosterol, β-sitosterol, stigmasterol, ergosterol, campesterol, α-sitostanol, α-sitostanol, stigmastanol, campestanol, cycloartenol, etc. and their fatty acid esters, ferulic acid ester, cinnamic acid ester, glycosides, and the like.

In the present invention, the amount of the phytosterol dissolved in the oil and fat composition is not particularly limited as long as it is in a dissolved state. From the standpoint of imparting a better cholesterol lowering effect than generally edible fats, the amount of the phytosterol dissolved in the oil and fat composition is 1.2% by weight or larger, preferably 2.0% by weight or larger, more preferably 2.5% by weight or larger. The upper limit thereof may be preferably less than 5 wt. %, in particular not more than 4.7 wt. %. Twenty wt. % or less, preferably 10 wt. % or less, of phytosterol is useful, which can be re-dissolved by being heated around a human body's temperature even after it has been dissolved by being heated in a oil or fat composition including a diacylglycerol and then has solidified wth precipitating crystals during storage.

As shown above, the diacyl glycerol (comprising less than 20 wt. % of triglycerides and less than 5 wt. % of monoglycerides) can be obtained with a high purity of 80 wt. % or more, being lightly colored with a little change in color by using an fatty acid obtained by steam-decomposing an oil or fat at 250 to 260° C. and distilling the decomposition product. In this method, however, phytosterol, which was included in an amount of about 0.05 to about 1.0 wt. % in the starting oil and fat, will be lost because of using the fatty acid which is distillable. A composition comprising such a diacyl glycerol has a decreased amount of phytosterol and for this reason it provides an inferior cholestrol-reducing effect to the natural oil or fat.

From the viewpoint where the lost phytosterol is supplemented and the effect to reduce the hemal cholesterol is produced, it is proposed that the amount of phytosterol dissolved in the oil or fat composition be 0.05 wt. % or more.

As phytosterol to supplement, the free one is advantageous to take from usual food products because a smaller amount of the supplemented one is sufficient to effect the cholestrol-reducing mechanism. In an oil or fat including 80 wt. % or more of a diacyl glycerol the free phytosterol is completely soluble at a normal temperature in an amount of up to 4.7 wt. %, with which an improved effect to reduce cholesterol is expected. From this viewpoint phytosterol to supplement is preferred to have a ratio of the free to the ester of 0.25 or more. It is added that the diacylglycerol obtained conventionally by chemical interesterification of an oil or fat and glycerin is easily degraded in color or others, having a value of 30 or more according to Lovibond Method, comprising less than 1 wt. % of phytosterol. When an excess of monoglycerides is distilled out of it, the free will be lost and the diacyl glycerol will have a ratio of the free to the ester of less than 0.25.

The oil or fat composition of the invention is suitable to a table cooking oil in use.

From the standpoint of providing a fat usable equally to generally edible fats, the oil and fat composition of the present invention preferably has a smoke point of 170° C. or higher. The content of monoacylglycerols in the fat composition is preferably 2% by weight or lower, more preferably 1.5% by weight or lower.

Further, an antioxidant is preferably added to the oil and fat composition of the present invention in an amount of 50 to 2,000 ppm for the purposes of storage stability and flavor stability, as in the case of generally edible fats. The antioxidant preferably comprises one or more members selected among natural antioxidants, tocopherol, tocotrienol, ascorbyl palmitate, ascorbyl stearate, BHT, BHA, phospholipids, etc. It more preferably comprises one or more members selected among natural antioxidants, tocopherol, tocotrienol, ascorbyl palmitate, phospholipids, etc.

The oil and fat composition of the present invention can be used similarly to generally edible oils and fats and is applicable to fat-processed foods. For example, it is usable in O/W type fat-processed foods such as drinks, desserts, ice creams, dressings, toppings, mayonnaises, and sauces for grilled meat; W/O type fat-processed foods such as margarines and spreads; processed fat foods such as peanut butters, fryings, and baking shortenings; processed foods such as potato chips, snack cakes, cakes, cookies, pies, breads, and chocolates; and other foods including bakery mixes, processed meat products, frozen entrees, and frozen foods.

It is also preferred to use the oil and fat composition of the present invention as a hypocholesteremic preparation in the form of a capsule, sugar-coated tablet, molded granules, candy, or drop.

Phytosterol increases the effect to reduce blood cholesterol by being dissolved in a diacylglycerol. It is noted that the diacylglycerol increases the effect to reduce blood cholesterol in case phytosterol exists in food, not being dissolved therein. The lipid ingredients of such a food include 15 wt. % or more of a diacylglycerol and phytosterol as co-component, which makes a food to reduce a blood cholesterol level. In the lipid ingredients of food, a weight ratio of a diacylglycerol to phytosterol may range from 0.5 to 200, preferably from 10 to 200, more preferably from 12 to 100, most preferably from 15 to 60.

The oil or fat composition of the invention will be below explained in details about application to an oil and fat-processed food product.

In the oil or fat-processed food product of the invention, an amount of oil and fat of the food product is preferred to range from 3 to 95 wt. % and that of phytosterol is preferred to range from 1 to 20 wt. %. The amount of the diacyl glycerol of the oil and fat may be 15 wt. % or more, preferably range from 15 to 95 wt. %, more preferably from 30 to 95wt. %, in particular preferably from 55 to 95 wt. %, most preferably from 80 to 95 wt. %.

The oil or fat-processed food product may be prepared by dissolving or dispersing phytosterol in oil or fat and adding it, alternatively adding phytosterol separately from oil or fat.

In the invention the oil or fat-processed food product is a processed food product of a mixture of the above shown oil or fat composition and other food material(s). The following is exemplified as the other food materials.

a) edible oil or fat each edible oil or fat shown above
   b) emulsifier proteins such as egg protein, soy bean protein, milk protein, protein separated from these proteins, protein such as (partial) decomposition products of these proteins, sucrose fatty acid ester, sorbitan fatty acid ester, glycerin fatty acid mono-ester, lecithin or an enzymaic decomposition product thereof.
   c) thickener thickening polysaccharides such as xanthane gum, gellan gum, guar gum, carageenan, pectine and Tragacanth gum and starches
   d) savorer such as table salt, sugar, vinegar and seasoning
   e) aroma such as spice and flavor
   f) colorant
   g) anti-oxidant such as tocopherol and natural anti-oxidant componetnts.

Preferable preparations are below shown about oil or fat-processed food product of the invention.

(1) Acidic Oil or Fat-processed Food Product of Oil-in-water Type
   a ratio of the oil phase to the aqueous phase; 20/80–80/20 (preferably 25/75–75/25)
   an amount of diacyl glycerol per the oil and fat of the oil phase; 15–95 wt. % (preferably 55–95 wt. %)
   an amount of phytosterol; 1–8 wt. % (preferably 2–5 wt. %)
   an amount of the emulsifier; 0.05 to 5 wt. % (preferably 0.1–3 wt. %) pH; 2–6 (preferably 3–5)

The pH can be adjusted with edible vinegar, an organic acid such as citric acid (or a salt thereof), a souring agent such as lemon juice. Using the above shown materials, preparations such as dressing and mayonnaise, of the oil-in-water type, acidic, oil or fat-processed food product, can be made conventionally, having the effect to reduce blood cholesterol and no prolem in appearance, flavor and feeling in taste.

(2) Plastic Oil or Fat-processed Food Product of Water-in-oil Type
   a ratio of the oil phase to the aqueous phase; 90/10–50/50 (preferably 80/20–65/35)
   an amount of diacyl glycerol per the oil and fat of the oil phase; 15–90 wt. % (preferably 55–90 wt. %)
   an amount of phytosterol; 1–7 wt. % (preferably 2–5 wt. %)
   the melting point of the oil or fat of the oil phase; 20–50° C. (preferably 20–40° C.)

It is preferred that the phytosterol of the product has nearly a size of less than 100 μm of needle-like crystals derived from the phytosterol (5 or less per 100 crystals) and the melting point of the needle-like crystals derived from the phytosterol is not more than 40° C.

Using the above shown materials, preparations such as margarin and spread, of the water-in-oil type, plastic, oil or fat-processed food product, can be made conventionally, having the effect to reduce blood cholesterol and no problem in feeling in taste and speadability.

(3) Potable, Oil or Fat-processed Food Product (Oil or Fat-processed Supplement)
   an amount of oil and fat; 3–30 wt. % (preferably 3–20 wt. %)
   an amount of diacylglycerol per the oil and fat; 15–95 wt. % (preferably 25–95 wt. %)
   an amount of phytosterol; 1–20 wt. % (preferably 5–20 wt. %)
   sugar; 40–90 wt. %
   blowing agent; 0–20 wt. %

Sugar such sucrose, glucose, maltose and fructose, a blowing agent such as a swelling agent such as sodium bicarbonate and an acidic agent such as tartaric acid, fumaric acid and citric acid are used.

Using the above shown materials, preparations such as tablets, candies and gummy, of the potable oil or fat-processed food product, can be made conventionally, having the effect to reduce blood cholesterol. The melting property in mouth is improved in particular by adding a blowing agent.

(4) Oil or Fat-including Beverage
   an amount of oil and fat; 0.2–10 wt. % (preferably 0.4–10 wt. %)
   an amount of diacyl glycerol per the oil and fat; 15–95 wt. %
   an amount of phytosterol; 0.2–1 wt. %
   sugar; 5–20 wt. %
   thickening stabilizer; 0.05–2 wt. %

(5) Baked Cookie
   an amount of oil and fat; 10–40 wt. % (preferably 20–35 wt. %)
   an amount of diacyl glycerol per the oil and fat; 15–95 wt. %
   an amount of phytosterol; 1–20 wt. % (preferably 1–15 wt. %)
   flour; 20–40 wt. %
   sugar; 5–25 wt. %
   egg; 5–20 wt. % table salt; 0.1–0.5 wt. % baking powder; 0–1 wt. %

EXAMPLES

In the Examples, the references to percentage are based on weight unless otherwise indicated.

PREPARATION OF DIACYLGLYCEROLS

Twenty grams of a commercial lipase preparation which was an immobilized lipase having the 1,3-position selectivity ("Lipozyme 3A"; trade name manufactured by Novo Industri A.S.) was mixed with 100 g of fatty acids obtained by decomposing rapeseed oil (fatty acid composition: 3.9% of palmitic acid, 1.7% of stearic acid, 57.0% of oleic acid, 21.9% of linoleic acid, and 12.8% of linolenic acid) and 15 g of glycerol. The mixture was reacted at 45° C. for 6 hours while the inside of the system was kept at a pressure of 5 mmHg absolute. The lipase preparation was separated from the resultant reaction mixture by filtration, and unreacted fatty acids and monoacylglycerols were separated by molecular distillation to give 72g of purified diacylglycerols (Prepared Sample 1). Prepared Sample 1 was an esterification composition of 0.7% of monoacylglycerol, 89.8% of diacylglycerol and 9.5% of triacylglycerol. It had a hue (10R+Y value, determined by the Lovibond method) of 16 and phytosterol content of 0%.

The esterification composition was analyzed by silylating each sample with an ester-silylating agent (e.g., Silylating Agent TH, trade name manufactured by Kanto Chemical), subsequently analyzing the silylation product with a gas chromatograph equipped with a capillary column (e.g., DB™—1; trade name manufactured by J & W) and having a flame ionization detector, and determining the composition from the retention times and peak area ratios.

changed in diacylglycerol concentration. The obtained mixture was heated and melted, then cooled at 5° C. In one week, precipitating phytosterol crystals were filtrated by a filter having a pore size of 0.45 μm and the amount of the dissolved phytosterol in the filtrate liquid was measured by gas chromatography. Results are shown in Table 1. It is noted from Table 1 that solubility of phytosterol increases drastically when the diacylglycerol content exceeds 15%.

TABLE 1

| Diacylglycerol content | 0 | 10 | 15 | 20 | 30 |
|---|---|---|---|---|---|
| Amount of dissolved phytosterol | 0.50 | 0.56 | 1.19 | 2.35 | 4.58 |

Examples 1 to 4 and Comparative Examples 1 to 3

Prepared Sample 1 was added to purified rapeseed oil to prepare fats containing the diacylglycerols in various concentrations. Further, a phytosterol ("Phytosterol"; trade name manufactured by Tama Biochemistry) was dissolved to give oil/fat composition A (Example 1), oil/fat composition B (Example 2), oil/fat composition C (Example 3; containing no purified rapeseed oil), oil/fat composition D (Example 4), and oil/fat composition E (Comparative Example 1) which contained the phytosterol in various concentrations. For comparison, oil/fat composition F obtained by adding only the phytosterol to purified rapeseed oil (Comparative Example 2) and oil/fat composition G obtained by adding the phytosterol and oleic acid as a solubilizer therefor to purified rapeseed oil (Comparative Example 3) were prepared. The composition and properties of each oil/fat composition and the results of evaluation for flavor as an edible fat are shown in Table 2.

TABLE 2

| | Components (parts by weight) | | | | | Diacylglycerol content | Phytosterol content | Appearance | Flavor |
|---|---|---|---|---|---|---|---|---|---|
| Ex. 1 (Fat composition A) | purified rapeseed oil (53 | + : | Prepared Sample 1 45 | + : | phytosterol 2) | 40.1% | 1.8% | transparent | no abnormality in taste and odor |
| Ex. 2 (Fat composition B) | purified rapeseed oil (32 | + : | Prepared Sample 1 65 | + : | phytosterol 3) | 59.4% | 2.8% | transparent | no abnormality in taste and odor |
| Ex. 3 (Fat composition C) | Prepared Sample 1 (95 | + : | phytosterol 5) | | | 85.1% | 4.7% | transparent | no abnormality in taste and odor |
| Ex. 4 (Fat composition D) | purified rapeseed oil (63 | + : | Prepared Sample 1 34 | + : | phytosterol 3) | 30.3% | 2.8% | transparent | no abnormality in taste and odor |
| Com. Ex. 1 (Fat composition E) | purified rapeseed oil (84 | + : | Prepared Sample 2 12 | + : | phytosterol 4) | 10.8% | 3.7% | opaque | no abnormality in taste and odor |
| Com. Ex. 2 (Fat composition F) | purified rapeseed oil (97 | + : | phytosterol 3 ) | | | 0.8% | 2.4% | opaque | no abnormality in taste and odor |
| Com. Ex. 3 (Fat composition G) | purified rapeseed oil (86 | + : | phytosterol 4 | + : | oleic acid 10) | 0.7% | 3.8% | transparent | abnormality in taste and odor |

1) By analysis with the aforementioned gas chromatograph.
2) In accordance with Standard Methods of Fat Analysis (Japan Oil Chemists' Society), 2.4.9.2 Sterol (Digitonin-bas chromatography).
3) Visual examination after storage at room temperature (25) for one week.
4) Sensory comparison with commercial purified fat.

5% of a phytosterol ("Phytosterol"; trade name manufactured by Tama Biochemistry) was added to a mixture of Prepared Sample 1 and purified rapeseed oil which had been

Example 5

Fifty-six examinees each having a fasting blood cholesterol level exceeding 220 mg/dl (average blood cholesterol level: 243.0 mg/dl) were divided into seven groups each consisting of eight members. The oil/fat compositions A, B, C, D, E and F described above and purified rapeseed oil were ingested as cooking oils by the examinees in meal in an amount of 10 g per day. The blood cholesterol concentrations were measured after 14-day ingestion and 28-day ingestion. The results are shown in Table 3.

TABLE 3

|  | Initial level (mg/dl) | After 14-day ingestion (mg/dl) | After 28-day ingestion (mg/dl) |
| --- | --- | --- | --- |
| Fat composition A | 239.88 ± 14.47 | 233.13 ± 16.15 | 229.25 ± 11.41 |
| Fat composition B | 248.75 ± 18.68 | 237.13 ± 19.12 | 232.25 ± 13.59* |
| Fat composition C | 243.50 ± 14.77 | 221.00 ± 25.89** | 220.86 ± 23.07** |
| Fat composition D | 247.90 ± 15.21 | 236.05 ± 17.85 | 232.16 ± 12.38* |
| Fat composition E | 240.50 ± 15.11 | 238.95 ± 17.50 | 236.20 ± 18.66 |
| Fat composition F | 238.75 ± 15.32 | 239.63 ± 18.08 | 235.63 ± 17.61 |
| Purified rapeseed oil | 241.75 ± 15.19 | 244.13 ± 22.36 | 240.75 ± 23.10 |

Significant difference from initial level *: $p < 0.05$ **: $p < 0.01$
±: SE

The groups who ingested oil/fat compositions B, C and D underwent a significant decrease in blood cholesterol concentration from the initial levels. In the group who ingested oil/fat composition A, a tendency to undergo a decrease in blood cholesterol concentration was observed although it was not a significant difference from the initial level. In the groups who ingested oil/fat compositions E and F and purified rapeseed oil, neither a significant decrease in blood cholesterol concentration from the initial level nor a tendency to undergo a decrease in the concentration was observed.

Example 6

Oil/fat compositions B, C, and G were used, after adding vitamin E in an amount of 400 ppm to each, to prepare cooking oils, which were then evaluated in cooking for fried pork cutlets. 300 g of each cooking oil was placed in a deep frying pan, and pork loin (120 g×2 pieces) having a coating consisting of egg, bread crumbs, and flour was cooked. The cooking oils were evaluated for smoking during cooking, workability, and the flavor, feeling on the tongue, and greasiness of the fried pork cutlets by five panelists in the following four grades using a commercial salad oil as a standard. The results are shown in Table 4.

Smoking
⊚ completely no smoking
○ almost no smoking
△ slight smoking
× smoking

Workability in cooking
⊚ excellent
○ good
△ slightly bad
× bad

Flavor
⊚ excellent
○ good
△ slightly bad
× bad

Feeling on the Tongue
⊚ excellent
○ good
△ slightly rough
× bad

Greasiness
⊚ extremely light
○ fairly light
△ slightly light
× not light at all

TABLE 4

|  | Smoking | Workability | Flavor | Feeling on the tongue | Greasiness |
| --- | --- | --- | --- | --- | --- |
| Fat composition B | ⊚ | ⊚ | ⊚ | ⊚ | ○ |
| Fat composition C | ⊚ | ⊚ | ⊚ | ⊚ | ○ |
| Fat composition G | × | × | × | △ | ○ |
| Commercial salad oil | ⊚ | ⊚ | ⊚ | ⊚ | ○ |

The cooking oil comprising oil/fat composition G smoked considerably due to the oleic acid serving as a phytosterol solubilizer, had poor workability, and gave fried pork cutlets with a strong irritant flavor. In contrast, the cooking oils comprising oil/fat compositions B and C were usable completely equally to the commercial salad oil.

Example 7

Using oil/fat composition C, brioches were prepared according to the following recipe. The following materials excluding oil/fat composition C were weighed and mixed by means of a mixer at a low speed for 30 seconds. Thereafter, oil/fat composition C was added and the mixture was mixed for 5 minutes at a low speed and for 22 minutes at a medium speed. The obtained dough was leavened at 27° C. for 30 minutes, and low-temperature leavening was further conducted at 5° C. for 15 hours. The resultant dough was divided into 37-g portions, which were shaped into a round form after an airing time of 15 minutes. The shaped dough was leavened at 33° C. and a humidity of 75% for 60 minutes and then baked at 190° C. for 9 minutes to prepare brioches.

| (Recipe for brioche) | |
| --- | --- |
| Flour (hard) | 100.0 parts by weight |
| Yeast | 5.0 parts by weight |
| Yeast food | 0.1 parts by weight |
| Sugar | 15.0 parts by weight |
| Salt | 2.0 parts by weight |
| Powdered skim milk | 4.0 parts by weight |
| Whole egg | 50.0 parts by weight |
| Fat composition C | 30.0 parts by weight |
| Water | 15.0 parts by weight |

Twelve examinees each having a fasting blood cholesterol level exceeding 200 mg/dl ingested the two above-prepared brioches (about 68 g; about 10 g in terms of fat composition amount) at breakfast each day for 10 days to examine the change in blood cholesterol level. As a result, it was found that although the average blood cholesterol level of the twelve examinees at the beginning was 232.81±19.01 mg/dl, the average blood cholesterol level thereof after 10-day ingestion was 211.53±23.49 mg/dl. Thus, a decrease in blood cholesterol value with a clear significant difference ($p<0.05$) was observed.

Example 8

Using decomposition fatty acids obtained from a mixture of palm oil and soybean oil, diacylglycerols (Prepared Sample 2) were obtained according to the process for preparing diacylglycerols described above. (Composition of Prepared Sample 2)

| Fatty acid composition | |
| --- | --- |
| Palmitic acid | 19.8% |
| Stearic acid | 4.1% |
| Oleic acid | 29.1% |
| Linoleic acid | 40.1% |
| Linolenic acid | 4.9% |
| Esterification composition | |
| Monoacylglycerols | 0.4% |
| Diacylglycerols | 88.3% |
| Triacylglycerols | 11.3% |

Oil/fat composition H was prepared by compounding Prepared Sample 2, a hardened rapeseed oil (iodine value: 89, melting point: 29° C.), and a phytosterol in a weight ratio of 30:67:3.

French fried potatoes were prepared using oil/fat composition H as a shortening for frying, and evaluated. Oil/fat composition H was fed in an amount of 10 kg into a fryer and heated to 180° C. Peeled potatoes were sliced, washed with water, dried by sopping, and heated for 3 minutes in the above fryer to prepare french fried potatoes. The oil content of these french fried potatoes was about 12%.

Subsequently, these french fried potatoes were used to determine their blood cholesterol lowering effect. Eight examinees each having a fasting blood cholesterol level exceeding 200 mg/dl were caused to ingest the above-prepared french fried potatoes in an amount of 100 g (about 12 g in terms of fat composition amount) in every evening meal for 10 days to examine the change in blood cholesterol level. As a result, it was found that although the average blood cholesterol level of the eight examinees at the beginning was 233.43±17.66 mg/dl, the average blood cholesterol level thereof after 10-day ingestion of the french fried potatoes was 219.37±20.81 mg/dl. Thus, there was a tendency for the blood cholesterol level to decrease.

Example 9 (Mayonnaise)

Preparation of Diacylglycerols

Using fatty acids obtained by decomposing soybean oil, diacylglycerols having the following composition (Prepared Sample 3) was obtained after conducting reaction and purification in the same manner as Example 1. (Composition of Prepared Sample 3)

| Fatty acid composition | |
| --- | --- |
| Myristic acid | 0.1% |
| Palmitic acid | 2.6% |
| Stearic acid | 0.8% |
| Oleic acid | 28.4% |
| Linoleic acid | 59.7% |
| Linolenic acid | 6.9% |
| Arachidinic acid | 1.2% |
| Eicosenoic acid | 0.3% |
| Esterification composition | |
| Monoacylglycerols | 0.8% |
| Diacylglycerols | 88.7% |
| Triacylglycerols | 11.5% |

Oil/fat compositions I and J of the present invention and oil/fat compositions K and L for comparison were obtained by adding Prepared Sample 3 and/or a phytosterol ("Phytosterol"; trade name manufactured by Tama Biochemistry) to purified soybean oil.

TABLE 5

| | Components (parts by weight) | Diacyl-glycerol content | Phyto-sterol content |
| --- | --- | --- | --- |
| Fat composition I | purified soybean oil + Prepared Sample 3 + phytosterol (4:92:4) | 81.7% | 4.2% |
| Fat composition J | purified soybean oil + Prepared Sample 3 + phytosterol (4:92:2) | 81.7% | 2.2% |
| Fat composition K | purified soybean oil + phytosterol (96:4) | 1.44% | 4.2% |
| Fat composition L | purified soybean oil + Prepared Sample 3 (8:92) | 81.7% | 0.3% |

Using the above oil/fat compositions, mayonnaise was prepared according to the following recipe.

Each oil/fat compositions I, K and L was dripped into an aqueous phase, while stirring, to conduct pre-emulsification. The pre-emulsion was homogenized by a homogenizer to prepare mayonnaise ①, ③ and ④ having the average particle size of 2.5 to 3.5 µm.

Separately, oil/fat composition J was dripped into an aqueous phase, while stirring, to conduct pre-emulsification. 2% of phytosterol powder was added to the pre-emulsion, then the pre-emulsion was homogenized by a homogenizer to prepare mayonnaise ② having the average particle size of 2.5 to 3.5 µm.

| (Recipe for mayonnaise) | |
| --- | --- |
| (Aqueous phase) | |
| Salt | 3.0 parts by weight |
| Best-purified sugar | 1.0 parts by weight |
| Seasoning (monosodium glutamate monohydrate) | 0.5 parts by weight |
| Spice (powdered mustard) | 0.3 parts by weight |
| Yolk | 14.0 parts by weight |
| Vinegar (10% acidity) | 8.0 parts by weight |
| Thickener | 0.5 parts by weight |
| Water | 22.7 parts by weight |
| (Oil phase) | |
| Oil/fat composition | 50.0 parts by weight |

Evaluation of Blood Cholesterol Concentrations

Forty examinees each having a fasting blood cholesterol level exceeding 220 mg/dl (average blood cholesterol level: 242.5 mg/dl) were divided into four groups each consisting of ten members. The mayonnaises ① to ④ described above were ingested in an amount of 20 g per day by the examinees in meal. The blood cholesterol concentrations were measured after 14-day ingestion. Results are shown in Table 6.

TABLE 6

|  | Initial level (mg/dl) | After 14-day ingestion (mg/dl) |
|---|---|---|
| Mayonnaise ① | 240.5 ± 5.6 | 228.5 ± 4.6* |
| Mayonnaise ② | 243.9 ± 8.0 | 234.4 ± 8.9* |
| Mayonnaise ③ | 242.9 ± 6.2 | 239.0 ± 8.6 |
| Mayonnaise ④ | 244.0 ± 7.2 | 241.1 ± 9.4 |

Significant difference from the initial level *: $p < 0.05$
±: SE

The groups who ingested mayonnaises ① and ② underwent a significant decrease in blood cholesterol concentration from the initial levels. In the groups who ingested mayonnaise ③ and ④, neither a significant decrease in blood cholesterol concentration from the initial level nor a tendency to undergo a decrease in the concentration was observed.

Evaluation of Appearance, Flavor and Feeling in the Mouth

The above mayonnaise was sensorily evaluated for texture, gloss, shape retention, flavor and feeling on the tongue by six panelists. A comparative evaluation was conducted among the four kinds of mayonnaise. Mayonnaises ①, ② and ④ had no problems at all, while mayonnaise ③ had roughness on the tongue. There was a problem on the feeling in the mouth when a phytosterol did not coexist with diacylglycerols.

Example 10 (Spread)

| (Recipe for Spread) | |
|---|---|
| (Oil phase) | |
| Oil and fat* | 65.4 parts by weight |
| Phytosterol | 2.7 parts by weight |
| Lecithin | 0.1 parts by weight |
| Monoglyceride | 0.5 parts by weight |
| Condensed ricinoleic ester | 0.5 parts by weight |
| Flavor | 0.1 parts by weight |
| (Aqueous phase) | |
| Water | 29.2 parts by weight |
| Powdered skim milk | 0.3 parts by weight |
| Salt | 1.3 parts by weight |

*Oil and fat; 66% of the above-described diacylglycerol (Prepared Sample 3)/31% of partial-hardened palm oil (IV = 40), oil's melting point: 34.8° C.

*Oil and fat; 66% of the above-described diacylglycerol (Prepared Sample 3)/ 31% of partial-hardened palm oil (IV=40), oil's melting point: 34.8° C.

The oil and aqueous phases described above were prepared, then mixed and emulsified for 10 minutes by a honomixer (manufactured by Tokushu Kika Kogyo). The resultant emulsion was rapidly cooled in a conventional manner to plasticize it. Thus, a spread was produced.

Evaluation

The quality of the obtained spread (feeling in the month and spreadability) was evaluated by special panelists. The spread products, both just after production and after storage for one month at 5° C., had no roughness, but were smooth in the mouth, and had a good meltability. They were easy to spread smoothly and thin on bread.

The particle size of spicular phytosterol crystals and melting temperature thereof were measured by an optical microscope equipped with a heat stage ("FP82HT" for the heat stage; "Olympus BX50" for the optical microscope). The spread products, both just after production and after storage for one month at 5° C., had no crystals of larger than 100 μm in the particle size and all the crystals were dissolved at 40° C. or below.

Example 11 (Tablet)

| (Recipe for Tablet) | |
|---|---|
| Xylitol | 45 parts by weight |
| Sorbitol | 44 parts by weight |
| Diacylglycerols (Prepared Sample 3) | 5 parts by weight |
| Phytosterol | 5 parts by weight |
| Flavor | 1 parts by weight |

Diacylglycerols and a phytosterol were mixed, heated and melted, then cooled. The obtained bulk product was pulverized and mixed with the other components. By tableting it in a conventional manner, tablet ① weighing 2g per piece was obtained. Separately, tablet ② was obtained according to the same process except for using soybean oil in place of diacylglycerols.

Evaluation of Blood Cholesterol Concentrations

Twenty adult, male examinees each having a fasting blood cholesterol level exceeding 200 mg/dl (average blood cholesterol level: 242.5 mg/dl) were divided into two groups each consisting of ten members. The tablets ① and ② described above were ingested by the examinees after supper by 4 pieces per day. The blood cholesterol concentrations were measured after 14-day ingestion. The results are shown in Table 7.

TABLE 7

|  | Initial level (mg/dl) | After 14-day ingestion (mg/dl) |
|---|---|---|
| Tablet ① | 248 ± 7.8 | 218 ± 5.2* |
| Tablet ② | 236 ± 5.4 | 238 ± 6.5 |

Significant difference from initial level *: $p < 0.05$
±: SE

Example 12 (Candy)

| (Recipe for Candy) | |
|---|---|
| Sugar | 33 parts by weight |
| Liquid sugar* | 48 parts by weight |
| Diacylglycerols (Prepared Sample 3) | 5 parts by weight |
| Phytosterol | 5 parts by weight |
| Citric acid | 3 parts by weight |

-continued

| (Recipe for Candy) | |
|---|---|
| Sodium bicarbonate | 5 parts by weight |
| Flavor | 1 parts by weight |

*Liquid sugar; MC45, manufactured by Nippon Shokuhin Kagaku (liquid sugar degree 70%; 45% of maltose and 25% of glucose)

Sugar and liquid sugar were mixed and heated to homogenize it. The other components were added thereto, and the mixture was casted into a mold in a conventional manner to prepare candies. Meltability of these candies having the blood cholesterol lowering effect was also improved.

Example 13 (Drink)

Using oil/fat composition C, a drink was prepared.

| (Recipe for Drink) | |
|---|---|
| (Oil phase) | |
| Fat/oil composition C | 10 parts by weight |
| Lecithin | 0.05 parts by weight |
| Sucrose fatty acid ester (low HLB) | 0.05 parts by weight |
| (Aqueous phase) | |
| Sugar | 20 parts by weight |
| Milk protein | 2 parts by weight |
| Fruit-juice extract | 5 parts by weight |
| Sucrose fatty acid ester (high HLB) | 0.05 parts by weight |
| Thickener | 0.1 parts by weight |
| Water | balance |

The above oily and aqueous phases were prepared and mixed for 20 minutes at 65° C. with a homomixer to conduct pre-emulsification, then homogenized by a homogenizer. The obtained emulsion was sterilized at super high temperature in a continuous sterilizing machine, and sterilizedly bottled. The resultant drink was drunken in smoothness through the throat.

What is claimed is:

1. An oil or fat composition, comprising an oil or fat comprising 15 wt. % or more of a diacylglycerol, 1.2 to 20 wt. % of phytosterol, and at most 2000 ppm of tocopherol, dissolved or dispersed in the oil or fat,
   wherein the amount of unsaturated fatty acids in the diacylglycerol is at least 70% by weight.

2. The composition of claim 1, comprising 15 to 95 wt. % of the diacylglycerol.

3. The composition of claim 1, comprising 30 to 95 wt. % of the diacylglycerol.

4. The composition of claim 1, comprising 80 to 95 wt. % of the diacylglycerol.

5. The composition of claim 1, comprising 1.2 to 10 wt. % of the phytosterol.

6. The composition of claim 1, comprising 1.2 to less than 5 wt. % of the phytosterol.

7. The composition of claim 1, comprising 1.2 to 4.7 wt. % of the phytosterol.

8. The composition of claim 1, which does not comprise the tocopherol.

9. The composition of claim 1, which does comprise the tocopherol.

10. A food product containing the oil or fat composition as defined in claim 1.

11. A hemal cholesterol-reducing pharmaceutical preparation including the oil or fat composition as defined in claim 1.

12. The food product as claimed in claim 11, which is a drink, a dessert, an ice-cream, a dressing, a topping, a mayonnaise, a flavoring sauce for grilled meat, a margarine, a spread, a peanut butter, a frying oil, a baking shortening, potato chips, a snack food, a cake, a cookie, a pie, a bread, a chocolate, a bakery mix, a processed meat product, a frozen entree or a frozen food.

13. The food product as claimed in claim 11, which is an oil or fat-processed food product of oil-in-water type or an oil or fat-processed food product of water-in-oil type.

14. A table cooking oil comprising an oil or fat composition as defined in claim 1.

15. A method of reducing a hemal cholesterol value comprising administering the oil or fat composition as defined in claim 1 to a person.

16. An oil or fat-processed food product comprising 3 to 95 wt. % of oil or fat comprising 15 wt. % or more of a diacylglycerol, 1 to 20 wt. % of phytosterol, and at most 2000 ppm of tocopherol, wherein the amount of unsaturated fatty acids in the diacylglycerol is at least 70% by weight.

17. A beverage product comprising 0.2 to 10 wt. % of an oil or fat comprising 15 wt. % or more of a diacylglycerol, 0.2 to 1 wt. % of phytosterol, and at most 2000 ppm of tocopherol, wherein the amount of unsaturated fatty acids in the diacylglycerol is at least 70% by weight.

* * * * *